(12) United States Patent
Dachowski

(10) Patent No.: US 8,393,022 B2
(45) Date of Patent: Mar. 12, 2013

(54) THIN-FILM SPLASH GUARD FOR A DENTAL CUSPIDOR

(76) Inventor: Damian D. Dachowski, Huntingdon Valley, PA (US)

( * ) Notice: Subject to any disclaimer, the term of this patent is extended or adjusted under 35 U.S.C. 154(b) by 490 days.

(21) Appl. No.: 12/246,331

(22) Filed: Oct. 6, 2008

(65) Prior Publication Data
US 2010/0086894 A1    Apr. 8, 2010

(51) Int. Cl.
*A47J 47/20* (2006.01)
*E03C 1/181* (2006.01)
*A61C 17/06* (2006.01)
*A61C 17/14* (2006.01)

(52) U.S. Cl. .................. 4/658; 4/263; 4/DIG. 9; 433/97
(58) Field of Classification Search ........... 4/658, 300.3, 4/DIG. 5, 258, 263, 264, DIG. 9; 433/97, 433/91, 116
See application file for complete search history.

(56) References Cited

U.S. PATENT DOCUMENTS

| | | | | |
|---|---|---|---|---|
| 1,626,689 A | * | 5/1927 | Pieper | ............................... 4/263 |
| 2,021,518 A | | 11/1935 | Pieper | |
| 2,489,967 A | | 11/1949 | Lavine | |
| 2,549,514 A | | 4/1951 | Oertel | |
| 2,644,956 A | | 7/1953 | Oertel | |
| 3,984,880 A | * | 10/1976 | Schrameyer | ...................... 4/609 |
| 4,663,035 A | * | 5/1987 | Rosander | ................. 210/167.01 |
| 4,716,602 A | * | 1/1988 | Brickhouse | ........................ 4/237 |
| 4,722,103 A | * | 2/1988 | Kliebert | ............................ 4/658 |
| 5,361,428 A | * | 11/1994 | Nanowsky et al. | ............... 4/558 |
| 5,462,434 A | * | 10/1995 | Mahr | .............................. 433/97 |
| 5,625,910 A | * | 5/1997 | Erickson et al. | ................. 4/658 |
| 5,732,416 A | * | 3/1998 | Albert | .......................... 4/300.3 |
| 7,178,177 B1 | * | 2/2007 | Valencia | ....................... 4/300.3 |
| 7,921,478 B1 | * | 4/2011 | Vanini | .......................... 4/300.3 |
| D657,060 S | * | 4/2012 | Frenkler et al. | .............. D24/177 |
| 2006/0090404 A1 | * | 5/2006 | Lovell | ............................... 52/97 |

OTHER PUBLICATIONS

Dictionary definition of "flaccid", p. 812, McGraw-Hill Dictionary of Scientific and Technical Terms (6th edition, 2003).*

* cited by examiner

*Primary Examiner* — Basil Katcheves
*Assistant Examiner* — Rodney Mintz
(74) *Attorney, Agent, or Firm* — Michael Crilly, Esq.

(57) ABSTRACT

A thin-film splash guard for use with dental cuspidors is described. The splash guard includes a thin-film sheet, a pair of slots, and an adhesive. The thin-film sheet is composed of a flexible, flaccid material with front and back surfaces which is sufficiently stiff when conformed to the shape of a dental cuspidor so as to extend above the side wall of the cuspidor. The slots are disposed from one edge of and along the thin-film sheet so as to generally define a center region and a pair of side regions. The adhesive is disposed along the front surface within each side region and or along the back surface within the center region. The thin-film splash guard is readily conformable to the shape and size of a cuspidor, easily attachable to the cuspidor in a removable fashion, and disposable.

6 Claims, 6 Drawing Sheets

THIN-FILM SPLASH GUARD FOR A DENTAL CUSPIDOR

CROSS REFERENCE TO RELATED APPLICATIONS

None.

FEDERALLY SPONSORED RESEARCH AND DEVELOPMENT

None.

BACKGROUND OF THE INVENTION

1. Field of the Invention

The invention generally relates to a splash guard for a dental cuspidor. Specifically, the invention is a flexible, thin-film splash guard which conforms to the shape of a cuspidor attached to a dental chair assembly. The splash guard secures to the cuspidor in an adjustable and removable fashion via a pair of slots and adhesive strips disposed along one edge of the guard. The splash guard is sufficiently stiff when conformed to the shape of a cuspidor so as to form a vertically disposed wall which extends above the cuspidor.

2. Background

A visit to the dentist invariably requires a patient to drink a liquid, typically water, without swallowing so as to remove blood, saliva, debris, and dental compounds from the mouth of the patient. This mixture of liquids, with or without solids, is expectorated by the patient into a dental cuspidor, also referred to as a basin.

FIG. 1 shows an exemplary cuspidor 25 attached to a dental chair assembly 20. A typical dental chair assembly 20 could include a console 21 and one or more support arms 23, 24 attached to a base 22 in a movable fashion adjacent to an adjustable chair. Support arms 23, 24 are further attached to a lamp, tray, and/or table. The console 21 further includes a bowl-shaped cuspidor 25 with rinse tube 26 and fill tube 27. The fill tube 27 is used to fill a cup 28 with water. The cuspidor 25 has a drain for the removal and disposal of liquids and solids deposited therein.

The accurate deposit of liquids and solids from a patient's mouth into a cuspidor is complicated by various factors. For example, some patients find it difficult to control the direction and/or velocity of a liquid expelled from the mouth even under the most optimum of conditions. Other patients find it difficult to control the direction and/or velocity of a liquid stream expelled from the mouth after a local anesthetic has been administered to the mouth region. Yet other patients have difficulty controlling the direction and/or velocity of a liquid stream expelled from the mouth when in a reclined or semi-reclined position. In all instances, the inaccurate control of a liquid stream, with or without solids, results in at least some of the liquid never reaching or remaining in the cuspidor, thereby contacting and contaminating the floor, walls, furniture, equipment, and/or dental assistant immediately adjacent to the patient. Liquid which fails to reach or to remain in the cuspidor presents health and/or safety hazards, and in some instances could delay or prevent the reuse of a procedure room and equipment therein. Accordingly, dental practices expend substantial time and financial resources to the cleanup of such liquids.

Several patents from the related arts are noteworthy. Shields are not conformable to a variety of cuspidor sizes and shapes. Furthermore, the described shields are re-usable, therefore requiring cleaning after each use.

Lavine, U.S. Pat. No. 2,489,967, describes a shield including a semi-circular sheet of plastic stock attached to plastic hooks. The shield is inserted into the interior of a cuspidor and held in place by the hooks.

Oertel, U.S. Pat. Nos. 2,644,956 and 2,549,514, describes a saliva apron composed of metal or clay for attachment to the rim of a conventional dental bowl. The apron partially traverses the peripheral area of a bowl and extends therefrom to increase the width of a bowl.

Pieper, U.S. Pat. No. 2,021,518, describes a rigid splash guard constructed and adapted to protect a cup against a liquid expelled from a patient's mouth or splashed from a cuspidor.

As is readily apparent from the discussions above, the related arts do not include a flexible, thin-film splash guard which is readily conformable to the shape and size of a cuspidor, easily attachable to a cuspidor in a removable fashion, and disposable after at least one use.

Accordingly, what is required is a flexible thin-film splash guard capable of preventing a liquid, with or without solids, from missing or otherwise splashing from a dental cuspidor.

SUMMARY OF THE INVENTION

An object of the invention is to provide a flexible thin-film splash guard capable of preventing liquid, with or without solids, from missing or otherwise splashing from a dental cuspidor.

In accordance with embodiments of the invention, the splash guard includes a thin-film sheet, a pair of slots, and an adhesive. The thin-film sheet is a planar or generally planar element composed of a flexible material with front and back surfaces. The thin film could be a flaccid material which is sufficiently stiff when conformed to a portion of a dental cuspidor so as to form a vertically disposed wall which extends above the cuspidor. The slots are disposed from one edge of the thin-film sheet so as to generally define a center region and a pair of side regions. The adhesive is disposed on the front surface within each side region and/or on the back surface within the center region.

In accordance with further embodiments of the invention, the thin-film sheet is transparent or translucent.

In accordance with other embodiments of the invention, the thin-film sheet is colored to provide a visual reference.

In accordance with yet other embodiments of the invention, the slots are sufficiently wide so that the center region contacts the interior of the dental cuspidor and the side regions contact the exterior of the dental cuspidor.

In accordance with still other embodiments of the invention, the slots are sufficiently long so that the center region contacts the interior of the dental cuspidor and the side regions contact the exterior of the dental cuspidor.

In accordance with still further embodiments of the invention, the thin-film sheet is composed of at least one polymer layer.

In accordance with still yet other embodiments of the invention, the thin-film sheet is composed of polystyrene.

In accordance with still yet further other embodiments of the invention, the adhesive is composed of an acrylic adhesive.

Several advantages are offered by the invention. The invention conforms to a variety of cuspidors which differ in size, shape, and design. The invention is easily and readily attachable to and removable from a dental cuspidor. The invention is a low-cost, disposable device which reduces the time and financial resources expended to cleanup contaminated liquids within a dental office.

| REFERENCE NUMERALS | |
|---|---|
| 1 | Splash guard |
| 2 | Slot |
| 3 | Slot |
| 4 | Width |
| 5 | Length |
| 6 | Adhesive region |
| 7 | Adhesive region |
| 8 | Center region |
| 9 | Side region |
| 10 | Side region |
| 11 | Fold region |
| 12 | Fold region |
| 13 | Adhesive region |
| 14 | Bottom edge |
| 15 | Top edge |
| 16 | Thickness |
| 17 | Height |
| 18 | Circumference |
| 19 | Side wall |
| 20 | Dental chair assembly |
| 21 | Console |
| 22 | Base |
| 23 | Support arm |
| 24 | Support arm |
| 25 | Cuspidor |
| 26 | Rinse tube |
| 27 | Fill tube |
| 28 | Cup |
| 29 | Front surface |
| 30 | Back surface |
| 31 | Interior surface |
| 32 | Exterior surface |
| 33 | Shield height |
| 34 | Sheet |
| 35 | Cover |
| 36 | Radius |

BRIEF DESCRIPTION OF THE DRAWINGS

The invention will now be described in more detail, by way of example only, with reference to the accompanying drawings, in which.

DETAILED DESCRIPTION OF THE INVENTION

Figure 1:
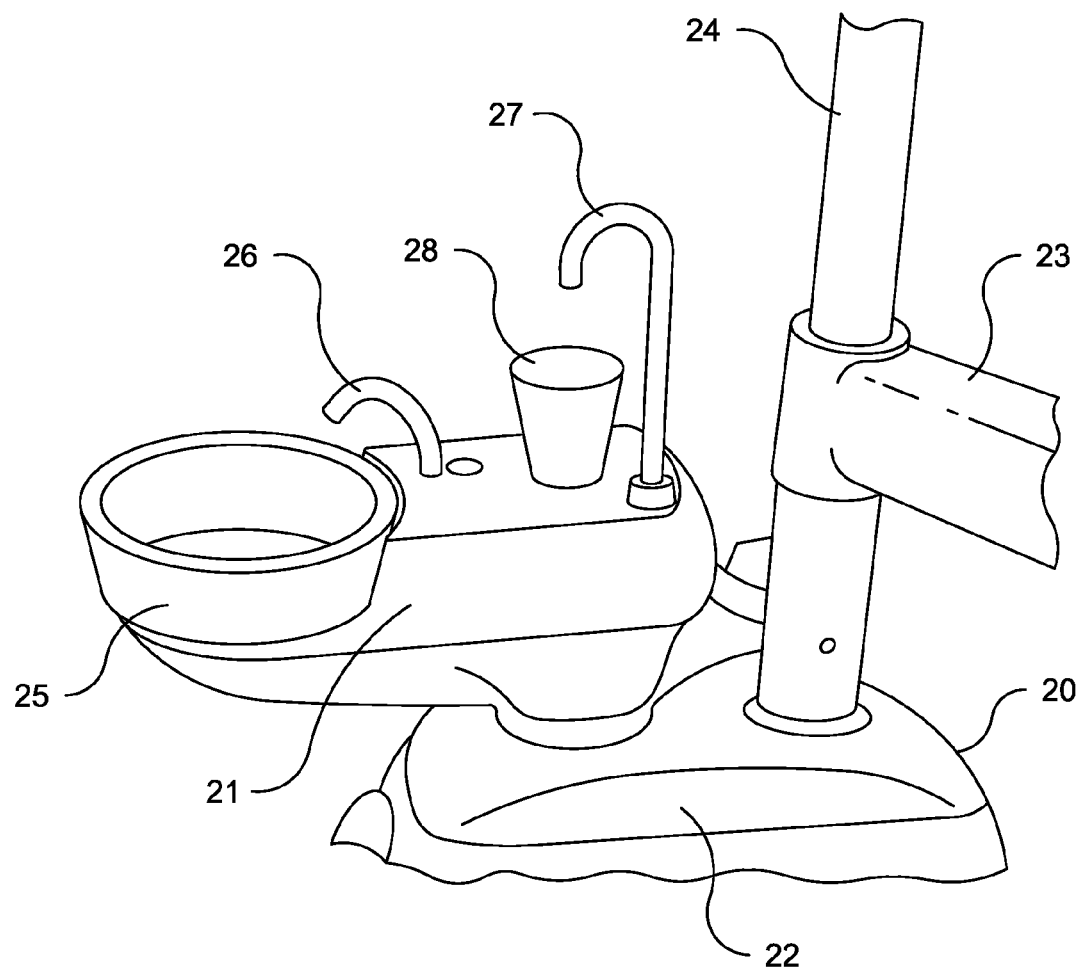
FIG. 1 is perspective view illustrating an exemplary dental cuspidor attached to a dental chair assembly.

Reference will now be made in detail to several preferred embodiments of the invention that are illustrated in the accompanying drawings. Wherever possible, same or similar reference numerals are used in the drawings and the description to refer to the same or like parts or steps. The drawings are not necessarily to precise scale.

Figure 2:
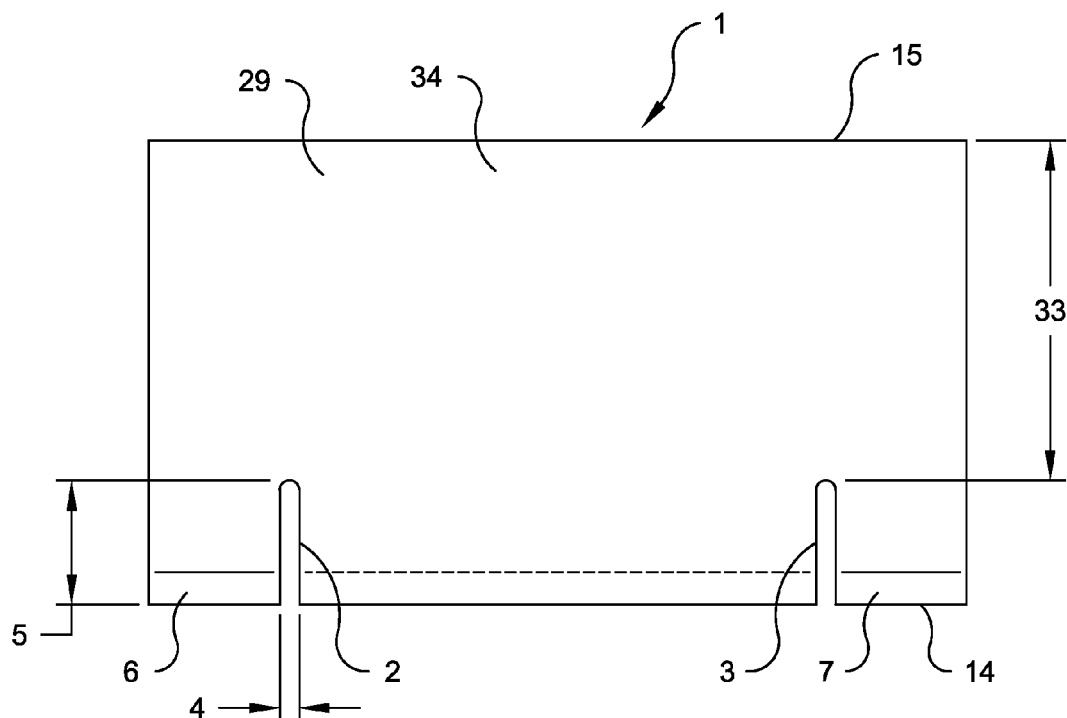
FIG. 2 is a plan view illustrating slots and adhesive regions along the front surface of a splash guard in accordance with an embodiment of the invention.
Figure 3:
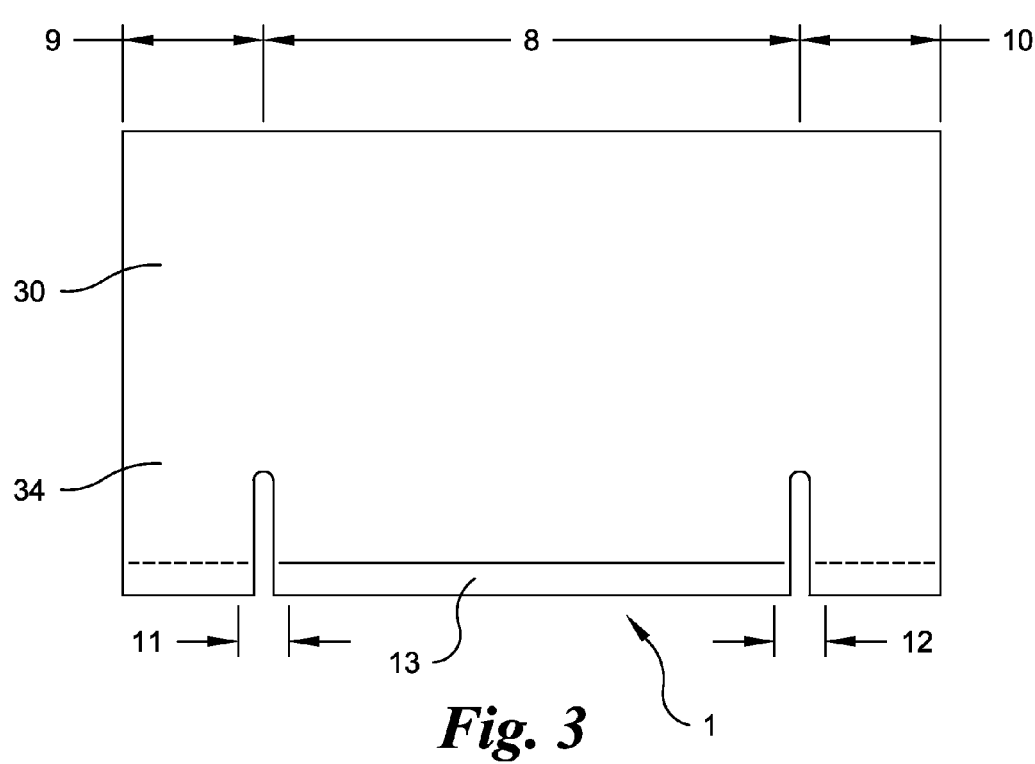
FIG. 3 is a plan view illustrating slots and adhesive region along the back surface of a splash guard and fold regions in accordance with an embodiment of the invention.

Referring now to FIGS. 2 and 3, the splash guard 1 is shown as a planar disposed sheet 34 of general rectangular shape and nominal thickness; however, other shapes are possible. The sheet 34 includes at least two slots 2, 3 and one or more adhesive regions 6, 7, 13. The splash guard 1 with slots 2, 3 could be die cut or punched from sheet or roll stock via known methods and techniques.

The sheet 34 is composed of a water-resistant polymer material, or the like, which is flexible, yet sufficiently rigid when curved, bent, or folded so as to remain in an upright orientation when vertically disposed. One exemplary material is polystyrene having a thickness of 2.5-mils. In preferred embodiments, the polymer material could be composed of a clear or translucent material to facilitate visual sightlines through the splash guard 1. In other embodiments, the sheet 34 could be composed of a clear, translucent or opaque material which is color coded, examples including, but not limited, to red, blue, and green, to provide a more distinctive visual reference about a cuspidor 25. In yet other embodiments, the sheet 34 could be composed of a polymer material which is flexible and flaccid, yet sufficiently rigid when curved, bent, or folded so as to remain upright when vertically disposed. For purposes of the described invention, flaccid is generally understood to refer to materials which are unable to retain an upright or vertical orientation when supported at a lower end, unless the material is curved, bent, or folded.

Slots 2, 3 facilitate the attachment of the splash guard 1 onto a cuspidor 25. Slots 2, 3 are generally rectangular shaped openings with a width 4 and length 5; however, other shapes are possible. Slots 2, 3 begin along the bottom edge 14 and partially extend across the sheet 34. The end of each slot 2, 3 could include a radius 36. In some embodiments, the slots 2, 3 could be oriented in a substantial parallel arrangement, as shown in FIGS. 2-3. In other embodiments, it might be advantageous to have at least one slot 2, 3 angled with respect to the bottom edge 14.

The slots 2, 3 generally define a center region 8 disposed between a pair of side regions 9, 10. The transition between the center region 8 and each side region 9, 10 constitutes a fold region 11, 12, respectively, which is at least as wide as the width 4 of each slot 2, 3.

Adhesive regions 6, 7, 13 facilitate the attachment of the splash guard 1 to a cuspidor 25. In some embodiments, a pair of adhesive regions 6, 7 could be provided along the front surface 29 of the sheet 34, so that one adhesive region 6, 7 is disposed along each side region 9, 10, respectively, adjacent to the bottom edge 14. In other embodiments, an adhesive region 13 could be provided along the back surface 30 of the sheet 34, so that the adhesive region 13 is disposed within the center region 8 adjacent to the bottom edge 14. In preferred embodiments, two adhesive regions 6, 7 are provided along the front surface 29 and one adhesive region 13 is provided along the back surface 30 of the sheet 34, as described herein.

Figure 7:
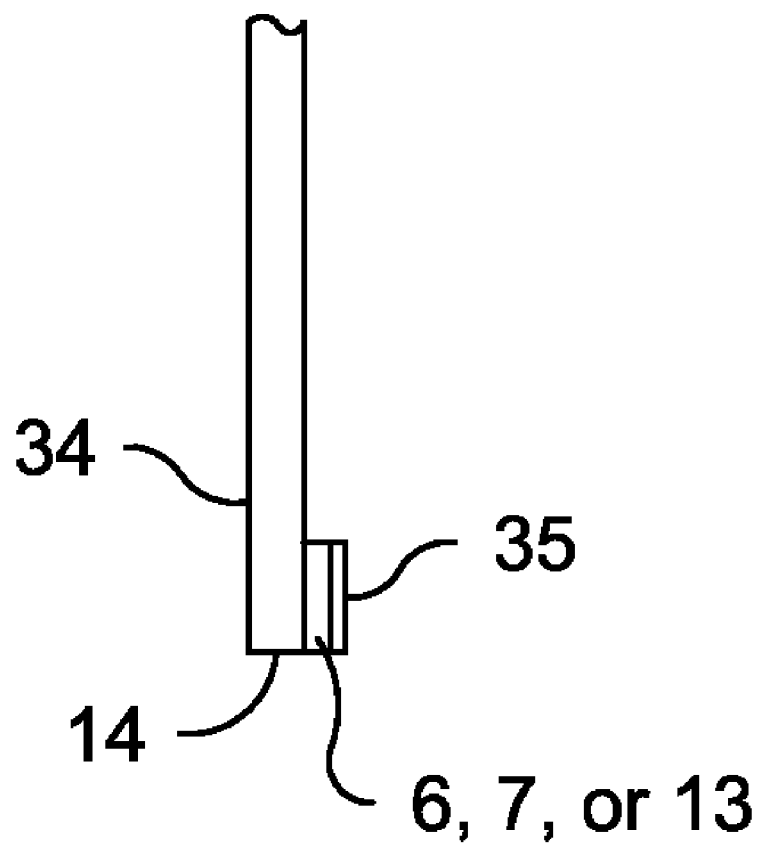
FIG. 7 is an enlarged section illustrating the arrangement of sheet, adhesive, and cover along the bottom edge of a thin-film splash guard in accordance with an embodiment of the invention.

The adhesive regions 6, 7, 13 are composed of a layer of adhesive material applied to the respective front and back surfaces 29, 30 of the sheet 34 via known methods and techniques. Adhesive regions 6, 7, 13 are preferred to reside at least along a portion of the area defined by the length 5. In preferred embodiments, adhesive regions 6, 7, 13 are rectangular, strip-shaped elements which are applied immediately along or adjacent to the bottom edge 14 and at least substantially traverse the region within which each resides. In other preferred embodiments, the adhesive regions 6, 7, 13 are protected by a cover 35 which contacts the adhesive opposite of the sheet 34 at the bottom edge 14, as represented in FIG. 7. The cover 35 is a strip-shaped element composed of paper, a thin film, a polymer, or the like which is removable from the adhesive prior to attachment of the splash shield 1 to a cuspidor 25. One exemplary material is a silicone coated polyester having a thickness of 1.5-mil.

Adhesives include compositions which readily bond to the sheet 34 in a non-removable fashion and also adhere to metal or ceramic in a secure, but removable manner. Compositions should be water resistant and provide excellent clarity and removability from glass. In preferred embodiments, the adhesive could be a water-based acrylic adhesive applied as a thin film or layer along the sheet 34, one example being adhesive no. WR-3800 used by Acucote, Inc. of Graham, N.C.

Figure 4:
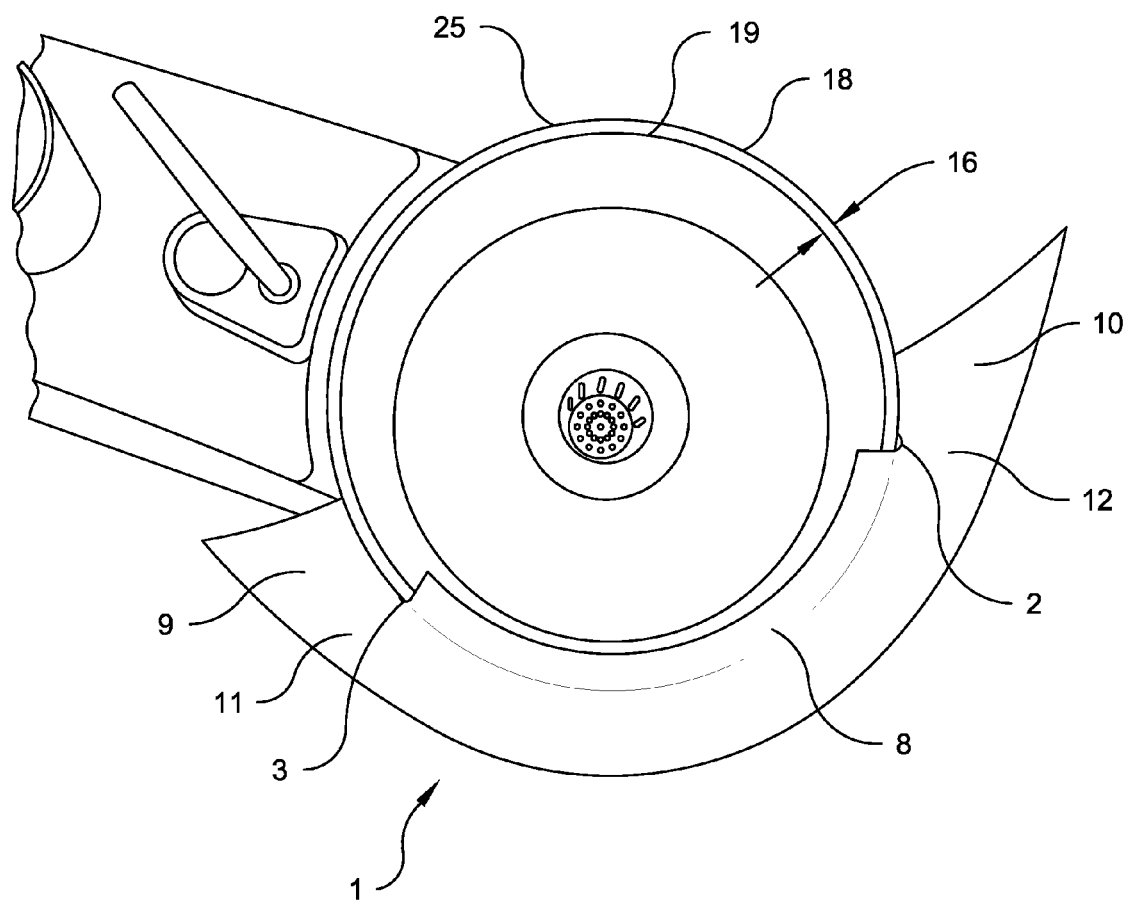
FIG. 4 is a top elevation view illustrating a thin-film splash guard disposed along a portion of the circumference of a cuspidor in accordance with an embodiment of the invention.
Figure 5:
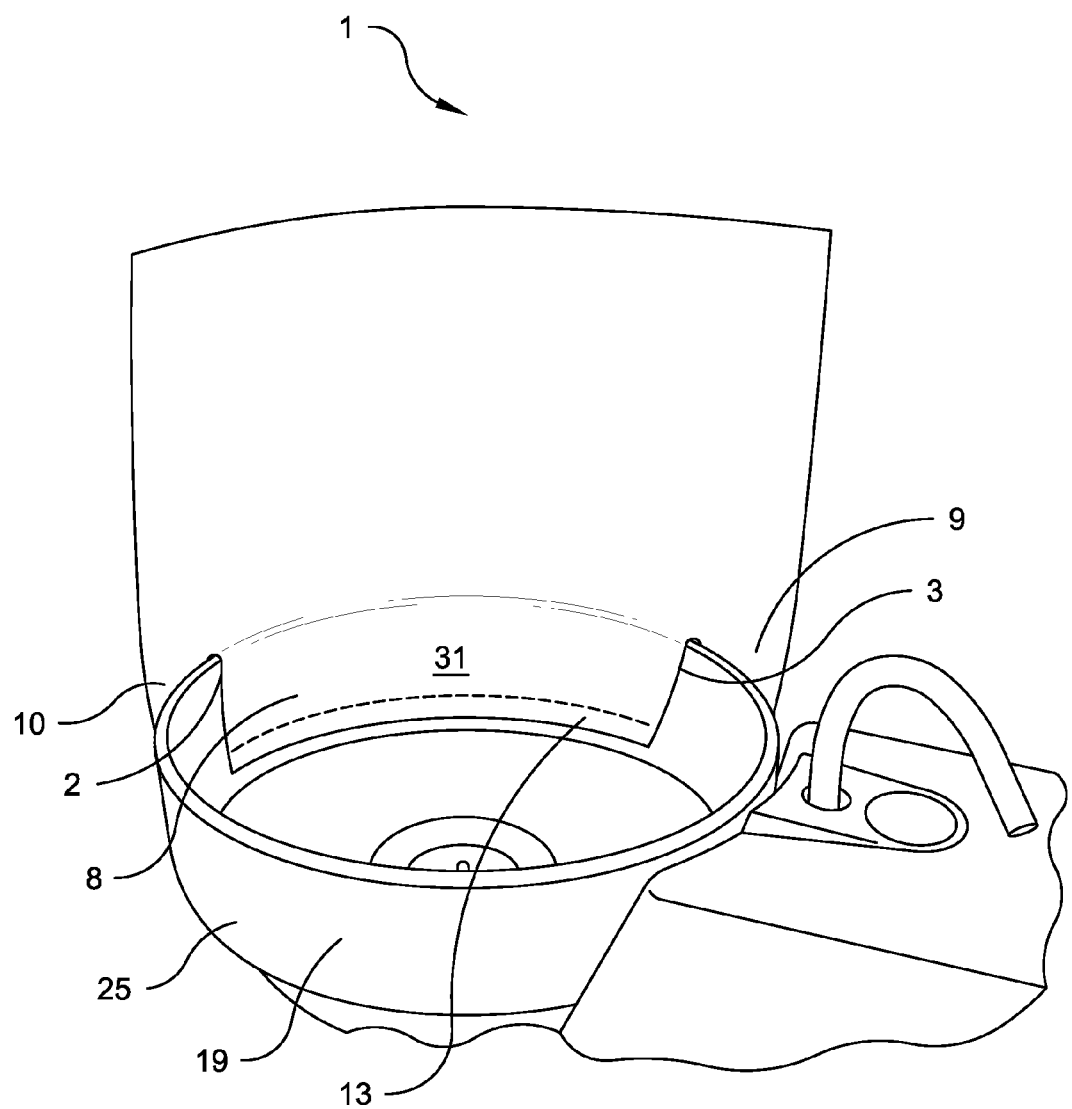
FIG. 5 is a perspective view illustrating a thin-film splash guard secured to a cuspidor so that a pair of slots along the guard is disposed about the side wall of the cuspidor in accordance with an embodiment of the invention.
Figure 6:
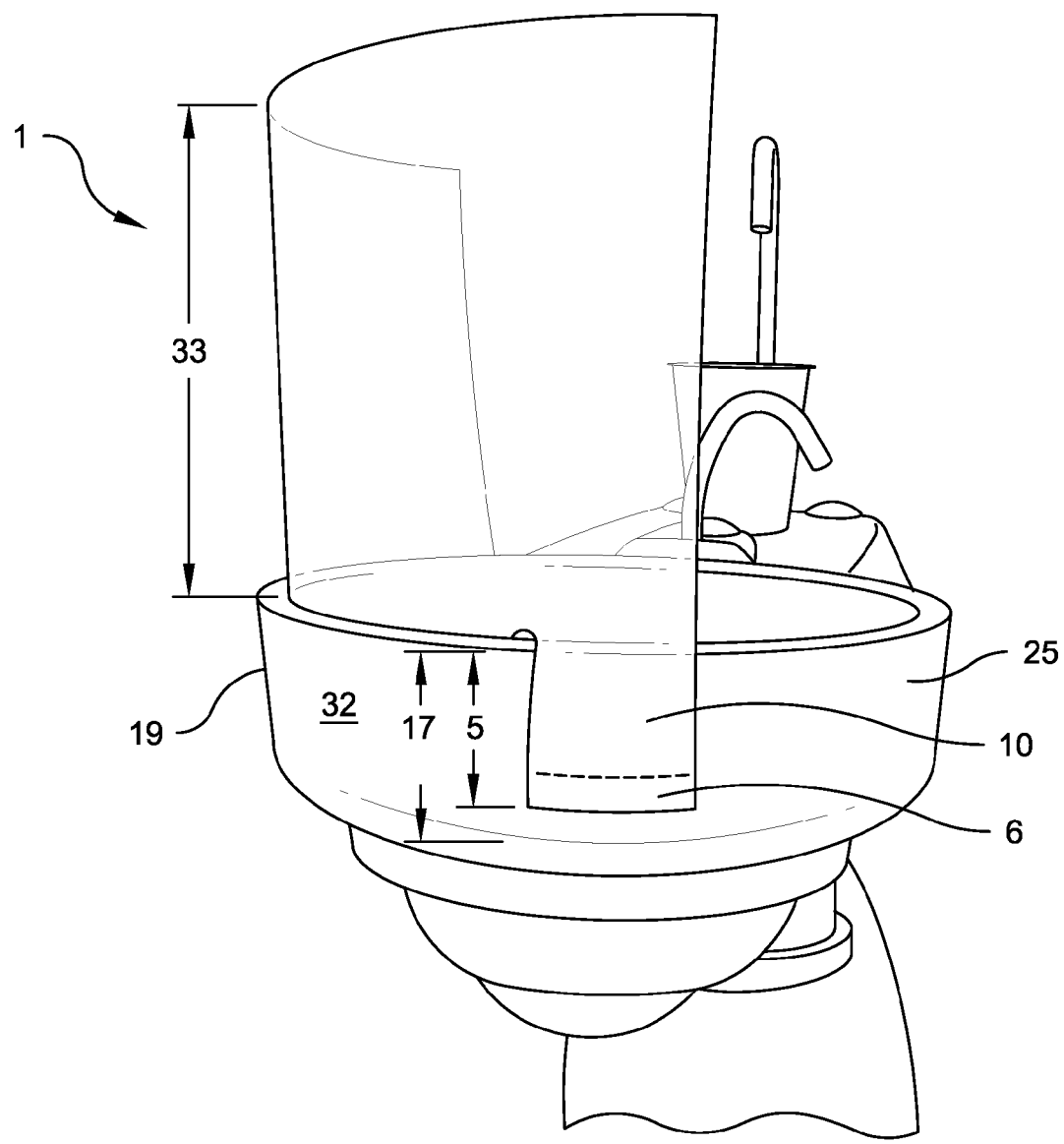
FIG. 6 is a side view illustrating the position of a side region of a thin-film splash guard along the side wall of a cuspidor and attachment of an adhesive region thereto in accordance with an embodiment of the invention.

Referring now to FIGS. 4-6, the splash guard 1 is shown attached to the side wall 19 and traverses the circumference 18 of a cuspidor 25. The splash guard 1 is preferred to partially traverse the circumference 18 so as to not interfere with proper use of the cuspidor 25 by a patient.

The attachment process requires the splash guard 1 to be partially folded, bent, or otherwise shaped along the fold regions 11, 12 so that the slots 2, 3 are disposed in an orientation which allows them to slide down onto and over the side wall 19. The width 4, as shown in FIG. 2, should be at least as wide as the thickness 16 of the side wall 19 to ensure a proper fit about the side wall 19. The center region 8 is disposed within the cuspidor 25 so that it contacts the interior surface 31 in a conformal fashion. The adhesive region 13 disposed along the back surface 30, as shown in FIG. 3, is pressed onto the interior surface 31 to secure the splash shield 1 to the side wall 19 of the cuspidor 25. The side regions 9, 10 are disposed outside of the cuspidor 25 so that each contacts the exterior surface 32 in a conformal fashion. The adhesive regions 6, 7 disposed along the front surface 29, as shown in FIG. 2, are pressed onto the exterior surface 32 to secure the splash guard 1 onto the side wall 19 of the cuspidor 25. The splash guard 1 could extend above the side wall 19 in a vertical or substantially vertical arrangement.

The splash guard 1 is removed from a cuspidor 25 by grasping an edge of the sheet 34 adjacent to one or both side regions 9, 10 and/or center region 8 and peeling the splash guard 1 away from the cuspidor 25 so as to separate the adhesive regions 6, 7, 13 from the cuspidor 25.

Referring again to FIGS. 2 and 6, the length 5 of each slot 2, 3 is preferred to be less than the height 17 of the side wall 19 so that the side regions 9, 10 contact the side wall 19 without overhang. The splash guard 1 extends above the cuspidor 25 by the shield height 33, generally defined as the distance between the top of at least one slot 2, 3 and the top edge 15.

Table 1 summarizes exemplary dimensions for one possible embodiment of the splash shield 1 composed of a transparent polystyrene composition.

| Dimension | Approximate Value |
| --- | --- |
| Sheet (34) - total width | 27.9 cm (11 inches) |
| Sheet (34) - total height | 19.1 cm (7.5 inches) |
| Side region (9) - width | 5.4 cm (2.125 inches) |
| Center region (8) - width | 17.1 cm (6.75 inches) |
| Side region (10) - width | 5.4 cm (2.125 inches) |
| Slot width (4) | 0.6 cm (0.25 inches) |
| Slot length (5) | 4.5 cm (1.75 inches) |
| Adhesive region (6) - width × height | 5.1 cm × 1.6 cm (2 inches × 0.625 inch) |
| Adhesive region (7) - width × height | 5.1 cm × 1.6 cm (2 inches × 0.625 inch) |
| Adhesive region (13) - width × height | 16.5 cm × 1.6 cm (6.5 inches × 0.625 inch) |
| Shield height (33) | 14.6 cm (5.75 inches) |

The description above indicates that a great degree of flexibility is offered in terms of the present invention. Although various embodiments have been described in considerable detail with reference to certain preferred versions thereof, other versions are possible. Therefore, the spirit and scope of the appended claims should not be limited to the description of the preferred versions contained herein.

What is claimed is:

1. A system, comprising:
  a dental cuspidor; and
  a splash guard, wherein said splash guard comprises:
  (a) a flaccid thin-film sheet composed of a material which is not stiff and therefore unable to retain an upright orientation when supported at a lower end unless curved, bent, or folded, said flaccid thin-film sheet having a front surface and a back surface;
  (b) a pair of slots which extend from one edge of said flaccid thin-film sheet and partially traverse said flaccid thin-film sheet, said slots define a center region disposed between a pair of side regions, said flaccid thin-film sheet conformally attached to said dental cuspidor so that said flaccid thin-film sheet extends upright from said dental cuspidor, said flaccid thin-film sheet disposed along a portion of a circumference of said dental cuspidor, wherein said center region contacts an interior surface of said dental cuspidor and said side regions contact an exterior surface of said dental cuspidor; and
  (c) an adhesive disposed along said back surface for adhering said flaccid thin-film sheet to said dental cuspidor.

2. The system of claim 1, wherein said adhesive is composed of an acrylic adhesive.

3. The system of claim 1, wherein said flaccid thin-film sheet is composed of polystyrene.

4. The system of claim 1, wherein said flaccid thin-film sheet is transparent or translucent.

5. The system of claim 1, wherein said flaccid thin-film sheet is colored.

6. A method of use for a splash guard comprising the steps of:
  (a) bending, curving, or folding a flaccid thin-film sheet during placement onto a dental cuspidor, said flaccid thin-film sheet composed of a material which is not stiff and therefore unable to retain an upright orientation when supported at a lower end unless curved, bent, or folded, said flaccid thin-film sheet having a front surface and a back surface, said flaccid thin-film sheet including a pair of slots which define a center region disposed between a pair of side regions;
  (b) placing said flaccid thin-film sheet onto said dental cuspidor, said bending, curving, or folding step ensures said flaccid thin-film sheet extends upright from said dental cuspidor, said flaccid thin-film sheet disposed along a portion of a circumference of said dental cuspidor, said center region contacting an interior surface of said dental cuspidor and said side regions contacting an exterior surface of said dental cuspidor; and
  (c) adhering an adhesive disposed along said back surface of said flaccid thin-film sheet to said dental cuspidor.

* * * * *